(12) United States Patent
Dooney, Jr. et al.

(10) Patent No.: US 11,931,241 B2
(45) Date of Patent: *Mar. 19, 2024

(54) EMBROIDERED TEXTILE SUPPORT A BIOLOGICAL GRAFT

(71) Applicant: Arthrex, Inc., Naples, FL (US)

(72) Inventors: Thomas Dooney, Jr., Naples, FL (US); Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1161 days.

This patent is subject to a terminal disclaimer.

(21) Appl. No.: 16/359,424

(22) Filed: Mar. 20, 2019

(65) Prior Publication Data

US 2019/0216593 A1 Jul. 18, 2019

Related U.S. Application Data

(63) Continuation of application No. 15/398,018, filed on Jan. 4, 2017, now Pat. No. 10,265,160.

(51) Int. Cl.
| | |
|---|---|
| *A61F 2/08* | (2006.01) |
| *A61B 17/04* | (2006.01) |
| *A61F 2/00* | (2006.01) |
| *A61F 2/40* | (2006.01) |
| *A61L 27/18* | (2006.01) |
| *A61L 27/36* | (2006.01) |
| *A61L 27/40* | (2006.01) |
| *A61L 27/50* | (2006.01) |
| *A61F 2/30* | (2006.01) |

(52) U.S. Cl.
CPC ........ *A61F 2/0811* (2013.01); *A61B 17/0401* (2013.01); *A61F 2/0063* (2013.01); *A61F 2/08* (2013.01); *A61F 2/40* (2013.01); *A61L 27/18* (2013.01); *A61L 27/36* (2013.01); *A61L 27/40* (2013.01); *A61L 27/50* (2013.01); *A61F 2002/30324* (2013.01); *A61F 2220/0075* (2013.01); *A61F 2230/0017* (2013.01)

(58) Field of Classification Search
CPC .. A61F 2/0811; A61F 2/08; A61F 2/40; A61F 2220/0075
See application file for complete search history.

(56) References Cited

U.S. PATENT DOCUMENTS

| | | |
|---|---|---|
| 4,517,687 A | 5/1985 | Liebig et al. |
| 5,990,378 A | 11/1999 | Ellis |
| 7,632,311 B2 | 12/2009 | Seedhom et al. |

(Continued)

FOREIGN PATENT DOCUMENTS

JP 2010517638 5/2010

OTHER PUBLICATIONS

Christopher Adams [online][retrieved on Jul. 12, 2022] (Retrieved form: YouTube: Arthrex Superior Capsular Reconstruction dated Feb. 20, 2015). [https://www.youtube.com/watch?v=Sff9QDRzyAs] publication year 2015, two figures.*

(Continued)

*Primary Examiner* — Bruce E Snow
(74) *Attorney, Agent, or Firm* — Carlson, Gaskey & Olds, P.C.

(57) ABSTRACT

A graft includes a biological graft. An embroidered textile supports the biological graft. Sutures attach the biological graft and the embroidered textile together.

11 Claims, 4 Drawing Sheets

(56) References Cited

U.S. PATENT DOCUMENTS

| | | |
|---|---|---|
| 7,758,643 B2 | 7/2010 | Stone et al. |
| 7,819,918 B2 | 10/2010 | Malaviya et al. |
| 7,871,440 B2 | 1/2011 | Schwartz et al. |
| 8,092,529 B2 | 1/2012 | Malaviya et al. |
| 9,226,992 B2 | 1/2016 | Mann et al. |
| 10,265,160 B2 * | 4/2019 | Dooney, Jr. .............. A61L 27/50 |
| 2003/0023316 A1 | 1/2003 | Brown et al. |
| 2008/0188936 A1 | 8/2008 | Ball et al. |
| 2010/0179591 A1 | 7/2010 | Saltzman et al. |
| 2011/0054610 A1 | 3/2011 | Ellis et al. |
| 2013/0116799 A1 * | 5/2013 | Derwin .................. A61L 27/34 |
| | | 623/23.72 |
| 2013/0296898 A1 | 11/2013 | Romuald |
| 2014/0343580 A1 | 11/2014 | Priewe |
| 2014/0379027 A1 * | 12/2014 | Dreyfuss ............ A61B 17/0401 |
| | | 606/228 |
| 2016/0361155 A1 | 12/2016 | Van Kampen |

OTHER PUBLICATIONS

International Preliminary Report on Patentability and Written Opinion for International Application No. PCT/US2017/068622 dated Jul. 18, 2019.

Teruhisa Mihata et al. "Clinical Results of Arthroscopic Superior Capsule Reconstruction for Irreparable Rotator Cuff Tears." Arthroscopy., vol. 29, No. 3, p. 459-470. Mar. 2013.

International Search Report and Written Opinion. Application No. PCT/US2017/068622, dated Apr. 12, 2018.

* cited by examiner

EMBROIDERED TEXTILE SUPPORT A BIOLOGICAL GRAFT

CROSS-REFERENCE TO RELATED APPLICATIONS

This application is a continuation of U.S. patent application Ser. No. 15/398,018, filed Jan. 4, 2017, the disclosure of which is incorporated by reference in its entirety herein.

BACKGROUND OF THE INVENTION

A shoulder joint is defined between a glenoid cavity of a scapula and a head of a humerus. In a Superior Capsule Reconstruction (SCR) procedure, biological grafts are employed to repair a tear in a rotator cuff of a shoulder joint.

To re-establish stability within a shoulder joint after injury, a dermal allograft can be employed to span the humerus and the glenoid cavity of the scapula and repair the rotator cuff. However, dermal allografts are not widely available. Autograft tissue is an alternative option, but it is not as strong as a dermal allograft. To compensate for this, larger autograft tissue can be employed to provide additional strength. However, this also increases the patient donor site morbidity as more tissue is needed.

SUMMARY

A graft includes a biological graft. An embroidered textile supports the biological graft. Sutures attach the biological graft and the embroidered textile together.

In an embodiment, the embroidered textile is formed of polyester.

In another embodiment, the embroidered textile is formed of polyester yarn with spaces located therebetween.

In another embodiment, the biological graft is an autograft.

In another embodiment, the biological graft and the embroidered textile each have a quadrilateral shape.

In another embodiment, the graft has a first width at a first end region, a second width at a second end region, and a length extending between the first end region and the second end region, and the first width is greater than the second width.

In another embodiment, the first end region of the graft is attached to the humerus with a suture anchor received in a hole in the humerus and at least one suture tape.

In another embodiment, the second end region of the graft is attached to the glenoid of the scapula with a suture anchor received in a hole in the glenoid and at least one suture tape.

In another embodiment, the first end is attached to a humerus, and the second end region is attached to a glenoid of a scapula.

In another embodiment, the embroidered textile and the biological graft have the same shape and the same size.

In another embodiment, the sutures that attach the embroidered textile and the biological graft together are located at each corner of the graft.

In another embodiment, the sutures that attach the embroidered textile and the biological graft together are located between each corner of the graft.

In another embodiment, the first end region and the second end region of the graft are each a reinforced portion formed by a thicker yarn or by a denser weave.

In another embodiment, a surgical repair assembly includes a graft including a biological graft. An embroidered textile supports the biological graft. Sutures attach the biological graft and the embroidered textile together. The graft has a first end region and a second end region. A first suture anchor is received in a first bone. A first suture secures the first end region of the graft to the first suture anchor and the first bone. A second suture anchor is received in a second bone. A second suture secures the second end region of the graft to the second suture anchor and the second bone.

In another embodiment, the first bone is a humerus and the second bone is a glenoid of a scapula.

In another embodiment, the embroidered textile is formed of polyester.

In another embodiment, the first end region and the second end region of the graft are each a reinforced portion formed by a thicker yarn or by a denser weave.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENTS

Figure 1:
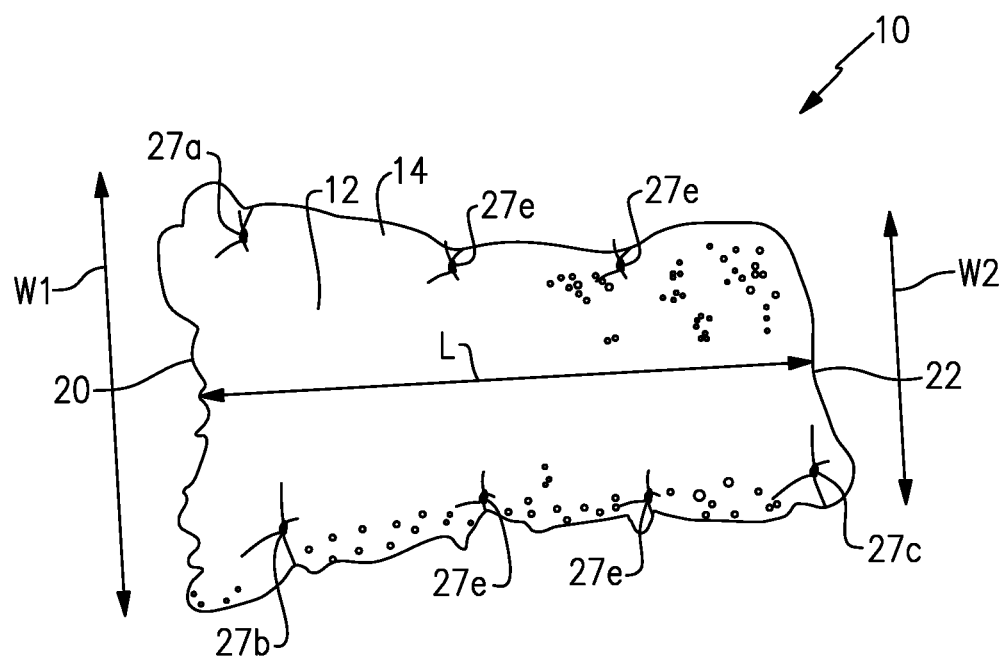
FIG. 1 schematically illustrates a bottom view of a graft including a biological graft supported by an embroidered textile.
Figure 2:
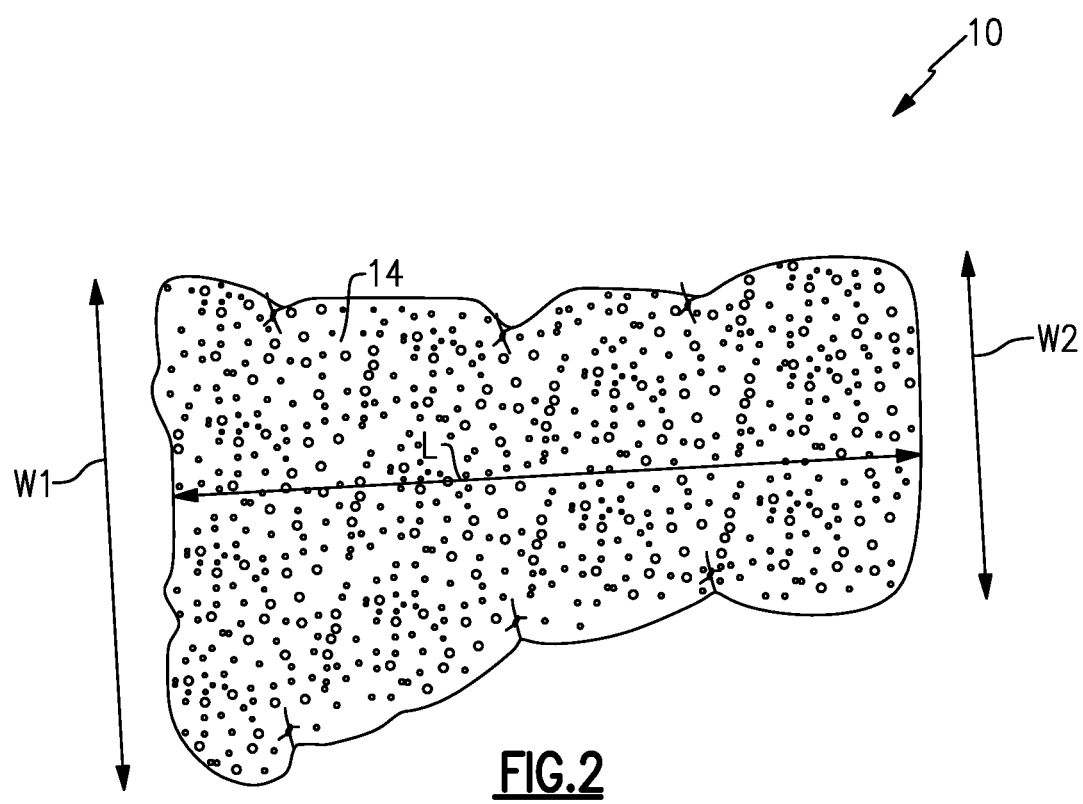
FIG. 2 schematically illustrates a top view of the graft.

FIGS. 1 and 2 schematically illustrate a graft 10 used to surgically repair a shoulder. The graft 10 includes a biological graft 12 supported by an embroidered textile 14. The graft 10 is not stiff and has some give.

The embroidered textile 14 can be embroidered from polyester yarn 16 to create a polyester patch. Spaces 18 are defined between yarn segments of the polyester yarn 16. The polyester yarn 16 can have any thickness or diameter. The density and pattern of the embroidered textile 14 can vary. The embroidered textile 14 has a tight mesh, which is less traumatic and abrasive to the body. The spaces 18 in the embroidered textile 14 promote tissue ingrowth and capture between the polyester yarn 16. During healing, tissue can grow into the spaces 18 in the embroidered textile 14, additionally securing the embroidered textile 14 to the body. In another example, the embroidered textile 14 can be a woven textile. The biological graft 12 and the embroidered textile 14 can have multiple dimensions, sizes, and thicknesses depending on the application, strength and required flexibility of the graft 10.

Figure 3:
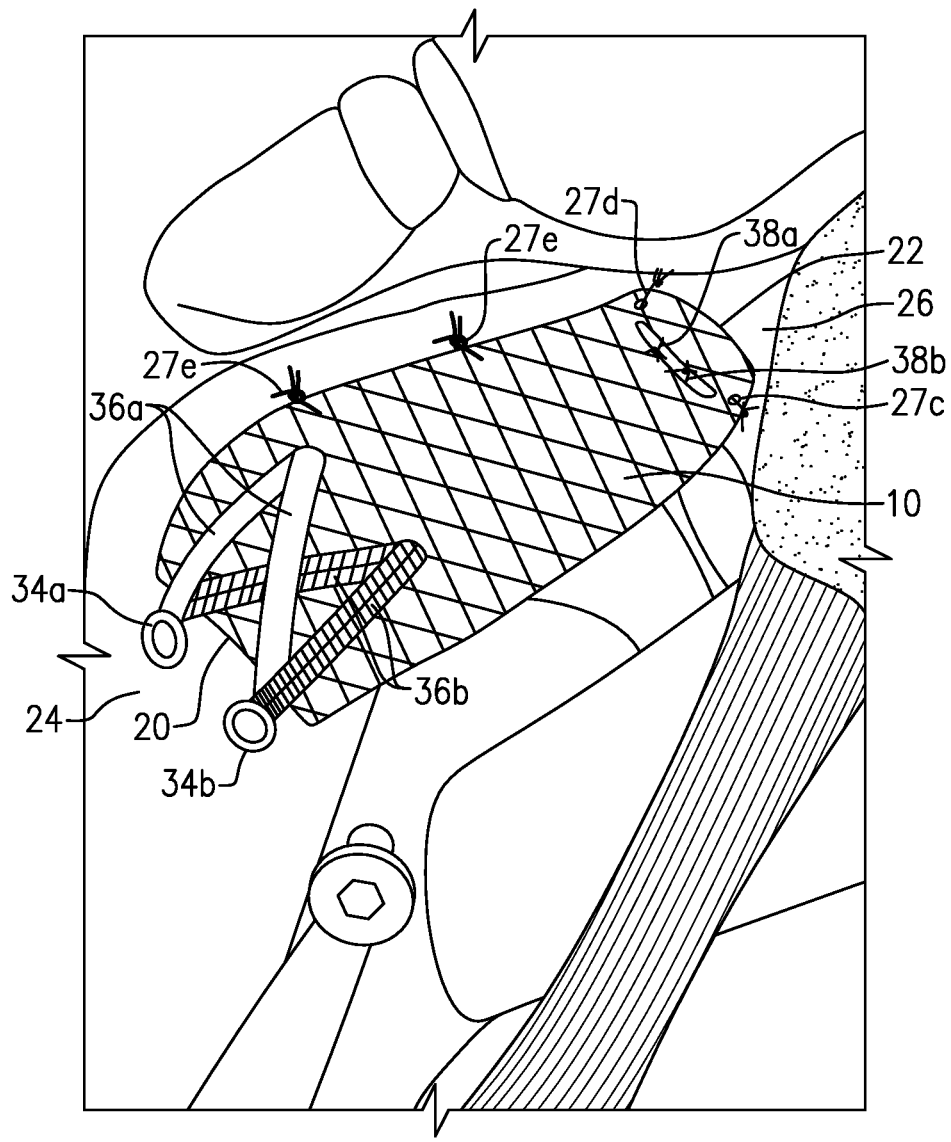
FIG. 3 schematically illustrates the graft attached to a shoulder joint.

The biological graft 12, such as autograft tissue, is harvested from a patient or cadaver. In one example, the biological graft 12 and the embroidered textile 14 both have a quadrilateral shape. The graft 10 has a length L of approximately 4 cm (1.58 inch), a first width W1 at a first end region 20 of approximately 2.5 cm (1 inch), and a second width W2 at a second end region 22 of approximately 2.0 cm (0.79 inch). The width W1 of the first end region 20 has a greater dimension than the width W2 of the second end region 22. As shown in FIG. 3, the first end region 20 of the graft 10 is attached to a humerus 24 of a shoulder, and the second end region 22 of the graft 10 is attached to the glenoid 26 of a scapula to repair a rotator cuff tear.

The embroidered textile 14 is attached to the biological graft 12. In one example, the embroidered textile 14 is attached to the biological graft by sutures 27. The embroidered textile 14 has roughly the same profile, shape, and size as the biological graft 12. In one example, the embroidered textile 14 and the biological graft 12 are attached at an outer perimeter. A suture 27a, 27b, 27c and 27d can be located in the vicinity of each corner of the graft 10 to secure the embroidered textile 14 to the biological graft 12. As shown in FIGS. 1 and 3, the sutures 27a, 27b, 27c and 27d wrap around an edge of each of the biological graft 12 and the embroidered textile 14. Sutures 27e can also be located at locations between the corners to further secure the embroidered textile 14 to the biological graft 12.

Figure 4:
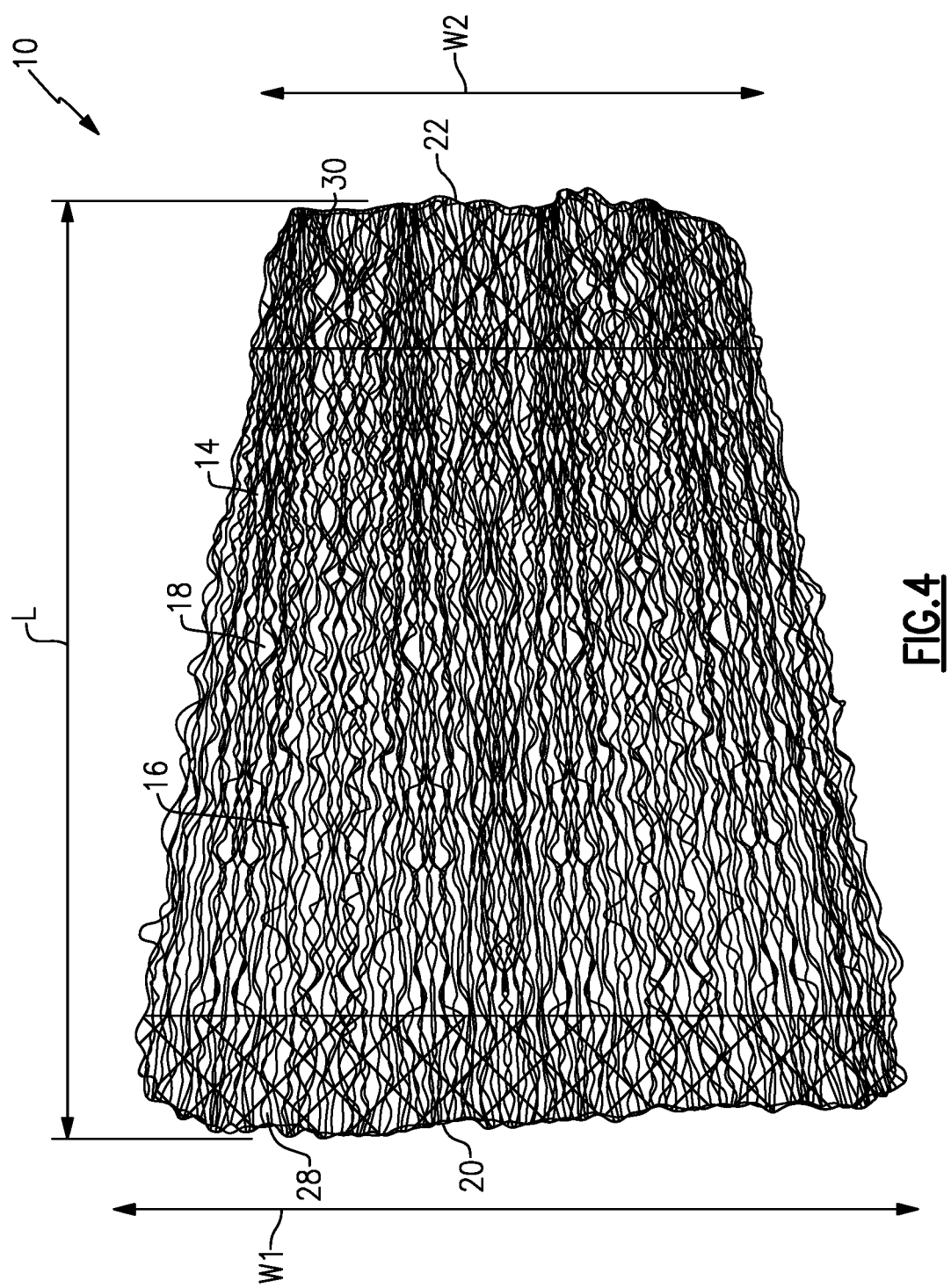
FIG. 4 schematically illustrates the graft with reinforced edges.

As shown in FIG. 4, in one example, the first end region 20 and the second end region 22 of the graft 10 are reinforced with additional material to form reinforced portions 28 and 30, respectively. The additional material strengthens the first end region 20 and the second end region 22 to prevent the sutures 36 and 38 (discussed below) from pulling through the graft 10 during attachment of the graft 10 to the humerus 24 and the glenoid 26 of the scapula, respectively. In one example, a thicker polyester yarn 16 is employed in the end regions 20 and 22 when creating the embroidered textile 14. In another example, the density of the polyester yarn 16 is greater in the end regions 20 and 22. That is, the end regions 20 and 22 can include more stitches and fewer spaces 18 than the remainder of the embroidered textile 14 to add strength to these regions.

Returning to FIG. 3, once the graft 10 is prepared, the first end region 20 of the graft 10 is attached to the humerus 24, and the second end region 22 of the graft 10 is attached to the glenoid 26 of the scapula. In one example, two holes are drilled in the humerus 24, and a suture anchor 34a and 34b is received in each hole in the humerus 24. Two first suture tapes 36a are attached to the humerus 24 by the first suture anchor 34a, and two second suture tapes 36b are attached to the humerus 24 by the second suture anchor 34b.

Two holes are drilled in the glenoid 26 of the scapula, and a suture anchor (not shown) is received in each hole. Two first sutures 38a are attached to the glenoid 26 of the scapula by the first suture anchor, and two second sutures 38b are attached to the glenoid 26 of the scapula by the second suture anchor.

Once the graft 10 is prepared, the two suture tapes 36a and 36b are passed through the first end region 20 of the graft 10, and the two sutures 38a and 38b are passed through the second end region 22 of the graft 10. One of the first sutures 36a and one of the second sutures 36b are attached to each other, leaving the other first suture 36a and the other second suture 38b free and unattached. The free and unattached strands of the first suture 36a and the second suture 36b are pulled to position the second end region 22 of the graft 10 on the glenoid 24 of the scapula. The other first suture 36a and the other second suture 36b are then tied.

The first suture tape 36a and the second suture tape 36b at the first end region 20 of the graft 10 are then employed to secure the first end region 20 of the graft 10 to the humerus 24. In one example, the first suture tape 36a and the second suture tape 36b are positioned in a cross pattern to increase strength. The suture tapes 36a and 36a are then employed to secure the first end region 20 of the graft 10 to the humerus 24.

The embroidered textile 14 strengthens the biological graft 12 and reinforces the repair. The embroidered textile 14 maintains the biological graft in its location long enough for healing, preventing the graft 10 from tearing away from a repair site prior to healing is complete. The embroidered textile 14 could either support or partially support/load-share the biological graft 12. The embroidered textile 14 supports the high loads, allowing the graft 10 to heal. Once the graft 10 has healed, the support from the embroidered textile 14 is no longer necessary.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A graft comprising:
    a biological graft, wherein the biological graft has a first width at a first end region, a second width at a second end region, and a length extending between the first end region and the second end region, and the first width is greater than the second width;
    an embroidered textile that supports the biological graft; and
    sutures that attach the biological graft and the embroidered textile together, wherein the first end region and the second end region of the embroidered textile are each reinforced relative to a remainder of the embroidered textile to define a reinforced portion, and the reinforced portion is formed by a thicker yarn or by a denser weave than the remainder of the embroidered textile.

2. The graft as recited in claim 1 wherein the embroidered textile is formed of polyester.

3. The graft as recited in claim 1 wherein the biological graft is an autograft.

4. The graft as recited in claim 1 wherein the biological graft and the embroidered textile each have a quadrilateral shape.

5. The graft as recited in claim 1 wherein the first end region of the graft is capable of attaching to the humerus with a suture anchor received in a hole in the humerus, and the second end region of the graft is capable of attaching to the glenoid of the scapula with another suture anchor received in a hole in the glenoid.

6. The graft as recited in claim 1 wherein the embroidered textile and the biological graft have the same shape and the same size.

7. The graft as recited in claim 1 wherein the sutures attach the biological graft and the embroidered textile together at an attachment location, and the attachment location is located at a corner of the biological graft and a corner of the embroidered textile.

8. The graft as recited in claim 7 wherein the attachment location secured by the sutures is located at each of four corners of the biological graft and the embroidered textile.

9. The graft as recited in claim 1 wherein the reinforced portion is formed by the thicker yarn than the remainder of the embroidered textile.

10. The graft as recited in claim 1 wherein the reinforced portion is formed by the denser weave than the remainder of the embroidered textile.

11. A graft comprising:
a biological graft having a first surface and an opposing second surface;
an embroidered textile that supports the biological graft; and
sutures that attach the biological graft and the embroidered textile together to form the graft having a first end region and a second end region;
a suture tape capable of attaching the first end region of the graft to a humerus with a suture anchor received in a hole in the humerus, wherein the suture tape is flat;
another suture is capable of attaching the second end region of the graft to the glenoid with another suture anchor received in a hole in the glenoid,
wherein the first end region and the second end region of the embroidered textile are each reinforced relative to a remainder of the embroidered textile to define a reinforced portion, and the reinforced portion is formed by a thicker yarn or by a denser weave than the remainder of the embroidered textile.

\* \* \* \* \*